United States Patent
Sádaba Champetier De Ribes et al.

(10) Patent No.: US 8,961,903 B2
(45) Date of Patent: Feb. 24, 2015

(54) MICROFLUIDIC DEVICE AND METHOD FOR FLUID CLOTTING TIME DETERMINATION

(75) Inventors: Iñaki Sádaba Champetier De Ribes, Zarautz (ES); Juan Antonio Peón Eguiguren, Donostia (ES)

(73) Assignee: Iline Microsystems, S.L., Donostia (ES)

( * ) Notice: Subject to any disclaimer, the term of this patent is extended or adjusted under 35 U.S.C. 154(b) by 906 days.

(21) Appl. No.: 12/678,661

(22) PCT Filed: Sep. 22, 2008

(86) PCT No.: PCT/EP2008/062642
§ 371 (c)(1),
(2), (4) Date: Jun. 8, 2010

(87) PCT Pub. No.: WO2009/037361
PCT Pub. Date: Mar. 26, 2009

(65) Prior Publication Data
US 2011/0039285 A1      Feb. 17, 2011

(30) Foreign Application Priority Data
Sep. 20, 2007   (EP) .................................... 07380258

(51) Int. Cl.
*B01L 3/00*       (2006.01)
*G01N 33/00*    (2006.01)
(Continued)

(52) U.S. Cl.
CPC .............. *G01N 33/86* (2013.01); *B01L 3/5027* (2013.01); *G01N 33/4905* (2013.01);
(Continued)

(58) Field of Classification Search
CPC ................ B01L 2300/0816; B01L 2300/0861; B01L 2300/0864; B01L 3/5027; B01L 3/502707; G01N 33/4905; G01N 33/86
USPC ................... 422/73, 500–504, 507, 516, 520; 436/180
See application file for complete search history.

(56) References Cited

U.S. PATENT DOCUMENTS 5,039,617 A   8/1991  McDonald et al.
5,100,727 A   3/1992  Kaneko et al.
(Continued)

FOREIGN PATENT DOCUMENTS

EP      0394070 B1     9/1994
JP      2003004752 A   1/2003
(Continued)

OTHER PUBLICATIONS

Japanese Office Action and English Translation, Jun. 13, 2013.

*Primary Examiner* — Dean Kwak
(74) *Attorney, Agent, or Firm* — Tristan A. Fuierer; Moore & Van Allen, PLLC

(57) ABSTRACT

A microfluidic passive device and a method for determining clotting time are described, of a fluid medium such as blood, of low production cost which can therefore be disposable. When optimised to determine blood clotting time, it requires a minimal whole blood sample (<5 μL) and it is particularly suited to INR or PT determination, which can be used autonomously by patient without venipuncture. Monitoring, and processing means to interpret the results are comprised in an external coagulometer device. A production method for the manufacture of the microfluidic device is also provided.

16 Claims, 13 Drawing Sheets

(51) Int. Cl.
*G01N 1/10* (2006.01)
*G01N 33/86* (2006.01)
*G01N 33/49* (2006.01)

(52) U.S. Cl.
CPC ... *B01L 3/502707* (2013.01); *B01L 2300/0816* (2013.01); *B01L 2300/0861* (2013.01); *B01L 2300/0864* (2013.01)
USPC ............ 422/503; 422/73; 422/500; 422/501; 422/502; 422/504; 422/507; 422/516; 422/520; 436/180

(56) References Cited

U.S. PATENT DOCUMENTS

| | | | |
|---|---|---|---|
| 5,110,727 A * | 5/1992 | Oberhardt | ........................ 435/13 |
| 5,298,224 A | 3/1994 | Plum | |
| 5,418,141 A | 5/1995 | Zweig et al. | |
| 5,447,440 A | 9/1995 | Davis et al. | |
| 5,504,011 A | 4/1996 | Gavin et al. | |
| 5,534,226 A | 7/1996 | Gavin et al. | |
| 5,625,036 A | 4/1997 | Hawkins et al. | |
| 5,628,961 A | 5/1997 | Davis et al. | |
| 5,866,425 A | 2/1999 | Woodhams et al. | |
| 6,699,718 B1 | 3/2004 | Bruegger | |
| 6,733,985 B1 | 5/2004 | Lee | |
| 6,750,053 B1 | 6/2004 | Widrig Opalsky et al. | |
| 6,900,021 B1 | 5/2005 | Harrison et al. | |
| 7,148,067 B2 | 12/2006 | Morrissey et al. | |
| 7,235,377 B2 | 6/2007 | Mann et al. | |
| 7,291,310 B2 | 11/2007 | Martin et al. | |
| 7,674,616 B2 | 3/2010 | Farnam, III et al. | |
| 7,736,901 B2 | 6/2010 | Opalsky et al. | |
| 7,867,771 B2 | 1/2011 | Okuda et al. | |
| 7,923,256 B2 | 4/2011 | Widrig Opalsky et al. | |
| 7,977,106 B2 | 7/2011 | Widrig Opalsky et al. | |
| 8,318,109 B2 * | 11/2012 | Saltsman et al. | ............... 422/502 |
| 2007/0122849 A1 | 5/2007 | Peekhaus et al. | |
| 2009/0162880 A1 | 6/2009 | Rechner | |
| 2009/0311675 A1 | 12/2009 | Hosokawa | |
| 2009/0317793 A1 * | 12/2009 | Jonsmann et al. | ................. 435/4 |

FOREIGN PATENT DOCUMENTS

| | | |
|---|---|---|
| WO | WO 92/21028 | 11/1992 |
| WO | WO 00/06761 | 2/2000 |
| WO | WO 02/48707 A2 | 6/2002 |
| WO | WO 2004/059316 A1 | 7/2004 |
| WO | WO 2007/025559 A1 | 3/2007 |

* cited by examiner

MICROFLUIDIC DEVICE AND METHOD FOR FLUID CLOTTING TIME DETERMINATION

CROSS-REFERENCE TO RELATED APPLICATIONS

This application is the U.S. national phase of PCT/EP2008/062642 filed Sep. 22, 2008, which claims priority of European Patent Application No. 07380258.9 filed Sep. 20, 2007.

FIELD OF THE INVENTION

The invention relates to a device of the type lab-on-a-chip and a method for determining clotting time of a fluid medium, in particular for determining blood clotting time. It also relates to a measuring device, such as a coagulometer, to be used in combination with the lab-on-a-chip of the invention.

BACKGROUND OF THE INVENTION

In healthy subjects, blood viscosity and thickness is regulated by a process known as hemostasis. This mechanism prevents loss of blood from the vascular system.

Blood coagulation is regulated by a complex process to stop any bleeding occurring in the body. Stable clots are formed through the interaction of coagulation protein factors, blood vessels and platelets. The process continues after healing, when the blood clot is dissolved.

During the first stages of clot formation, platelets aggregate, at the same time as a phenomenon known as blood cascade is activated. In this process, fibrinogen, a soluble plasma protein, is converted to an insoluble fibrin mesh or blood clot. This conversion is catalysed by thrombin, an enzyme generally present in blood in its inactive form, prothrombin.

Blood disorders arise from imbalances in hemostasis. These can be of a genetic origin, such as in hemophilia or Von Willebrand's disease; triggered by other conditions such as antiphospholipid antibody syndrome, irritable bowel syndrome or cancer; or acquired through extrinsic factors: patients taking oral anticoagulants as treatment or prophylaxis of thrombotic disorders, cardiac or vascular diseases.

Oral anticoagulant therapy, such as warfarin, is widely used and need frequent monitoring because of its narrow therapeutic index. The dosage should be adjusted periodically, in order to avoid thrombosis or risk of bleeding.

For these and other patients with known predisposition conditions such as immobility, obesity, mediation, or undergoing surgery or dental treatment, the availability of reliable tests enabling them to regularly monitor coagulation at their homes would represent a convenient, fast and cheap alternative to the clinic coagulation tests currently available. Such tests may also be employed as a preliminary aid in the diagnosis of hemostatic disorders.

The world's most common coagulation analysis is the so-called International Normalised Ratio (INR). This ratio is calculated through the Prothrombin Time (PT), which is the time elapsed from activation by the coagulating agent to the start of blood clotting. The activation agent is a tissue factor or thromboplastin and this mechanism is called the "extrinsic" pathway. Because of differences between different batches and manufacturers of tissue factor (it is a biologically obtained product), the INR was devised to standardise the results. The INR is the ratio of a patient's prothrombine time to the mean prothrombin time (MNPT) of at least 20 healthy normal people, raised to the power of the international Sensitivity Index (ISI) value for the control sample used. Each manufacturer gives an ISI for any factor tissue commercialised, indicating how the particular batch of tissue factor compares to an internationally standardized sample.

There is a second, but less commonly used analysis type, which consists of an analogous coagulation mechanism, through the "intrinsic" pathway, and it is called the Activated Partial Prothrombin Time (APTT). Both of these analyses are referred to as clotting times in the present application.

Traditionally, in Europe, these analyses were carried out in laboratories, where blood sample preparation is usually required prior to determining the PT. In recent years an emerging trend to employ Point-of-Care (POC) devices, or similarly named Nearly-Patient-Testing (NPT), to be used directly by the nurse or physician, or autonomously by the patient, has taken place and has largely replaced traditional methods.

The methods that were developed initially and known in the art required extraction of large or exact volumes of blood by venipuncture, subsequent treatment of blood prior to running the test and expert personnel to perform the process and interpret the results. In contrast, Point-of-care coagulometers, also known as portable coagulometers, require a whole blood droplet extracted by fingerpricking and provide immediate INR results.

Patent application WO 92/21028 describes a detection method based on ferromagnetism. The device contains a coagulation chamber and a control chamber, each of which is fitted with an agitating vane, which rotates in an oscillating magnetic field. The rotation of the vane in the coagulation chamber slows down as the coagulation of blood starts and exerts resistance against its movement. The coagulation time is measured as the time at which the relative movement of the agitation vanes in the chambers changes.

Other devices, such as those in U.S. Pat. No. 5,110,727 contain a blood sample with metallic particles dispersed through it. When an oscillating magnetic field is applied, a back and forth movement of the particles is induced that slows down as blood coagulates. The decrease in speed correlates to the increase of blood sample viscosity or the start of coagulation.

Patent application WO 00/06761 and WO 02/48707 A2 describe both a device fitted with electrodes in contact with a stationary blood sample and measure, respectively, the variation in electrical conductivity and current as blood viscosity increases.

WO 2004/059316 A1 describes a low cost, disposable device for determining clotting time of blood. The device is fitted with a microsensor, at least partially in contact with the fluid and measures the impedance and capacitance of the blood in the channel when blood coagulates and the flow stops.

However, high production costs associated with these devices restrict their use as disposable units.

Therefore, there remained a need for accurate, low cost disposable chips and detection methods for POC and/or NPT clotting time determination.

There has been a development towards detection tests of smaller size, requiring smaller and unmeasured whole blood samples, in the microliter scale, due to the advances in materials science and in electronic and optical methods.

Patent Application WO 2007/025559 A1 discloses a multi-layer device for the determination of coagulation in a plasma or whole blood sample, comprising one or more detection areas, all of them provided with at least one coagulation stimulation reagent.

Patent application US2007/0122849A1 discloses a sample assay structure in a microfluidic chip for quantitative analysis and detection of analytes.

EP 0394070 B1 describes a microfluidic device of one capillary channel, optimised for determining the APTT in a whole blood sample, of 40 µL of volume and residence time of 200 s. The device uses as reagent a mixture of an activated agent for activated partial thromboplastin time measurements and a mixture of phospholipids. The detection method employed through the capillary track is visual or optical, such as a LED, and determines the APTT when the blood flow stops along the device.

U.S. Pat. No. 6,900,021 describes a microfluidic device to conduct in vitro studies on the reaction and effects of various compounds on cells. The fluid flow is controlled using pumps, pressure differences or electrical fields, and not by capillarity in the microfluidic channel. There are two inlet flow paths intersecting and merging with a main flow path to allow the reaction to occur. Therefore, the main flow path does not comprise an area containing a reagent. Further, the reagents are not present in the chip, but added at different points and times, this allows the chip to be used for different reaction assays with different reagents.

Despite these developments, the point of care coagulometers being used today still have important drawbacks:
- although most of the chips or test strips used are disposable, they include several components such as means to collect the blood sample, means to measure the change in conductivity or means for measuring the change in viscosity. The presence of active components such as electrochemical contacts or oscillating particles in the strip makes the production of the disposable chip complex and expensive. Further, the size cannot be reduced without compromising the quality of the strip.
- Although advances have been made concerning the amount of blood sample needed for the test, the volume is still in the range of 10 µl in the best of cases, which is still inconvenient for the patient. This compares unfavourably, for example, with the amount used for other tests such as glucose measuring, which can be accurately done with a sample of blood of 1 µl or less.
- The detection and measuring apparatus that are used with the known test strips or chips are still rather complex. In some cases they need additional means to convey or move the blood sample, such as magnetic fields or pumps. In others the device needs several detection means: electrochemical or magnetic means to measure some property changes in the sample that require calibration chips, and additional detection means to read additional on-board quality control systems. This increases the complexity and therefore the cost of the portable device.

In view of these drawbacks, it is an object of the present invention to provide an improved microfluidic device and method for determining clotting time in a fluid medium such as blood or plasma, which involves only minimal steps, has a low cost, and can thus be used autonomously by the patient. It is another object to provide a measuring device to be used with the microfluidic device, such as a coagulometer, in order to detect and monitor the clotting time of the sample and the quality controls present in the microfluidic device, which is simple to manufacture, is compact and can be autonomously used by the patient.

SUMMARY OF THE INVENTION

In a first aspect the present invention provides a low cost microfluidic device for determining clotting time in a fluid medium such as blood or plasma, according to independent claim 1.

In a second aspect, the present invention provides a coagulometer device comprising a slot for introducing the microfluidic device, means for detecting and/or monitoring at least one property of a fluid medium and means for processing the data delivered by said detecting and/or monitoring means for the determining the clotting time of said fluid, according to independent claim 19.

In a third aspect the present invention provides a method for determining clotting time in a fluid medium, according to independent claim 25.

In a further aspect the present invention provides a method for manufacturing a microfluidic device for determining clotting time in a fluid medium, according to independent claim 26.

Favourable embodiments of the invention are defined in the dependent claims.

The present invention thus provides an improved microfluidic passive device of low production cost and simple use, which therefore can be disposable, for determining clotting time of a fluid. In addition, the microfluidic device (test strip), measuring device (coagulometer) and method according to the invention, provide accurate means for determining Prothrombin Time with a minimal sample of blood, and thus can be easily and autonomously used by the patient without requiring venipuncture.

These and other aspects of the invention will be apparent from and elucidated with reference to the embodiments described hereinafter.

BRIEF DESCRIPTION OF THE DRAWINGS

The invention will be better understood and its numerous objects and advantages will become more apparent to those skilled in the art by reference to the following drawings, in conjunction with the accompanying specification in which.

Throughout the figures like reference numerals refer to like elements.

DETAILED DESCRIPTION OF THE INVENTION

Figure 1:
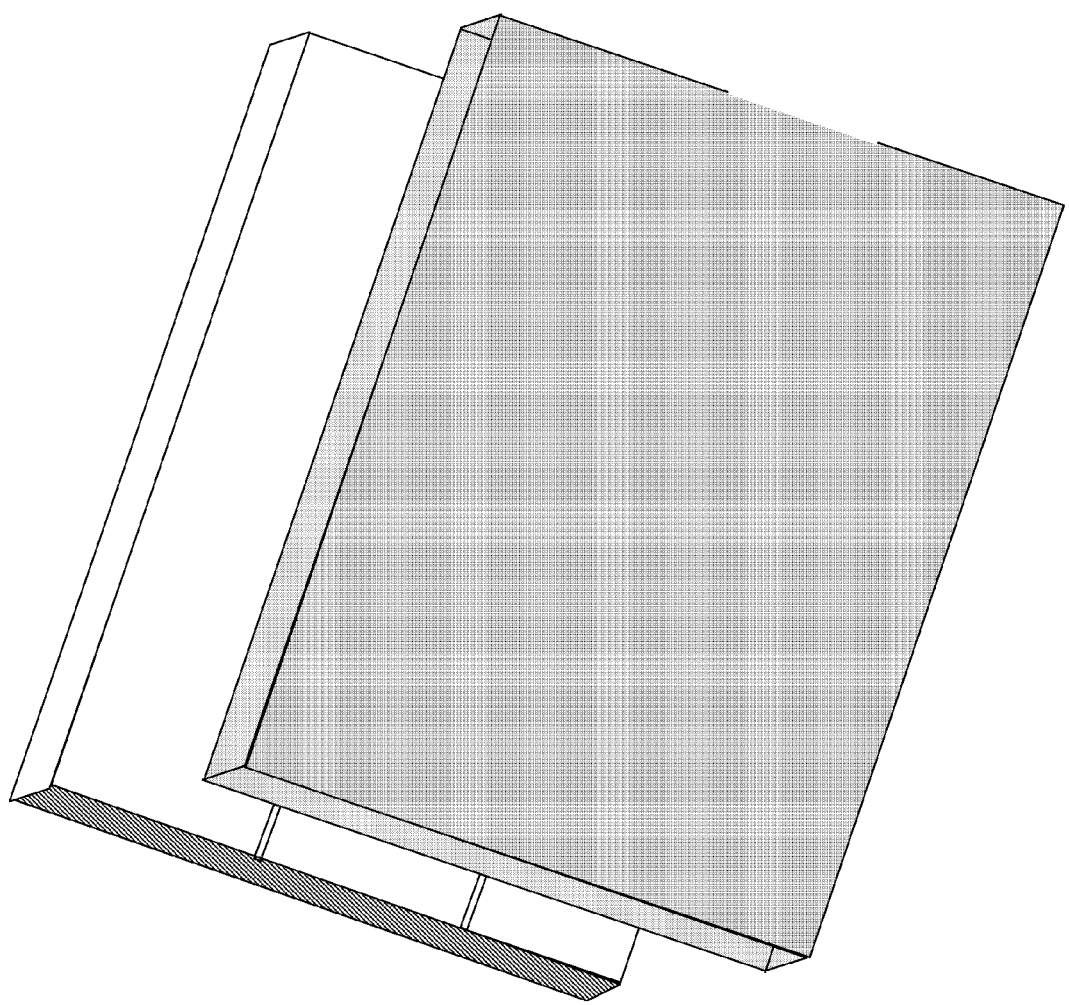
FIG. 1 shows an exploded perspective view of an embodiment of the device of the present invention, showing the two layers separately.

The present invention provides a device in the form of a chip or disposable test strip, for determining clotting time of a fluid, such as blood and plasma, a measuring apparatus to be used as portable coagulometer with the test strip of the invention, and a method of determining clotting time using the microfluidic device of the invention.

A Portable coagulometer, as a Point-of-care device, is a technology that follows four main lines of improvements: cost reduction, blood sample reduction, quality control and enhanced portability. All these four aspects are especially important for economically and reliably spreading patient self-testing.

The present invention has significant advantages with respect to the current state-of-the-art portable test strips and coagulometers:

Cost reduction: the disposable microfluidic chip is an extremely simple (passive) component, manufactured with high-volume low-cost production technologies and materials.

Blood sample reduction: blood samples well below 5 µL can be tested through the microfluidic chip technology with the necessary quality controls and accuracy.

Quality control: A number of distinct on-board quality controls can be integrated on the disposable device of the invention and read by a single detector means. In addition, the device allows the use of calibrated plasmas as external quality control.

Enhanced portability: the detection systems are extremely compact, low-cost and can be embedded on thin portable devices.

The invention is based on the fact that an appropriate microfluidic channel allows for the capillary flow of the fluid sample, such as blood or plasma, allowing the position or the velocity of the fluid front to be accurately monitored with simple means, in a passive way, without contact with the sample fluid. Rheological changes of the sample fluid upon the initiation of the clotting cascade (when the sample makes contact with the clotting reagent), and in particular the apparent viscosity changes at the clotting endpoint, have a significant effect on the monitored dynamical parameters.

These parameters can be monitored with the same simple detection means, and compared either with a control sample that does not contain a clotting reagent, or contains a different control reagent, or alternatively with a predicted theoretical value.

Without willing to be bound by theory, we believe that the microfluidic system of the invention mimics in some way the microcapillary structure of blood vessels and the dynamics of flowing blood. Due to the complexity and high sensitivity of blood coagulation stages (initiation, amplification, propagation and clot formation) it is highly favourable to reproduce as close as possible the in-vivo hemostasis environment. According to a published report from the University of Chicago [Kastrup, C. J. Runyon, M. K. Shen, F. Ismagilov, R. F. *Modular chemical mechanism predicts spatiotemporal dynamics of initiation in the complex network of hemostasis*, Department of Chemistry and institute for Biophysical Dynamics, University of Chicago, Edited by George M. Whitesides, Harvard University.], a microfluidic in vitro environment can mimic the actual blood clotting behaviour in human capillaries, which they proof is critical for the determination of the clotting times.

In addition, this invention allows continuous monitoring of the flow dynamics so that hemostasic molecular changes can be detected, providing high accuracy and reproducibility. In particular, the formation of the first insoluble fibrins has a measurable effect on the rheological properties due to the size of the microcapillary structure.

As shown in FIG. 1, in one embodiment the microfluidic device of the invention is a two-layer assembly comprising a lower planar substrate and a cover layer. On the lower substrate a sample distribution system is patterned, resulting in a series of channels or conducts, connected through one end by appropriate means to a sample introduction area.

The channels induce the flow through capillarity. The skilled person will be able to adjust the size and form of the channel patterned on the lower substrate to obtain a flow position or velocity which can be monitored with accuracy. To create the capillary flow of the fluid sample, a hydrophilic surface is needed in the channel, so that sufficient negative pressure is induced. This hydrophilic surface can be present on the lower substrate or on the cover layer.

In one embodiment the lower substrate is made of plastic. If the plastic is hydrophobic, the hydrophilicity in the channel has to be induced by means known to the skilled person such as a chemical treatment, chemical coating or plasma treatment, to obtain the desired surface energy or contact angle.

In a preferred embodiment, the hydrophilic surface is brought by the cover layer that seals the microfluidic channels patterned on the lower layer. In this embodiment, either a hydrophilic material is selected as cover layer, or is material which is subjected to a hydrophilic treatment as described above.

Alternatively, in a preferred embodiment, the hydrophilic properties are provided to the top layer by the adhesive used to bond the two layers that form the chip. In such a case it is important that the adhesive coating selected does not react with the fluid sample or interferes with the clotting reaction.

Therefore, the cover layer may consist of adhesive polymer films of various types, such as heat seals and pressure sensitive adhesives. Hydrophilic formulations, with added surfactants within the adhesive, can be employed. Hard adhesives are preferred, to prevent channel blockage due to adhesive flow during the sealing step or due to creep.

Figure 2:
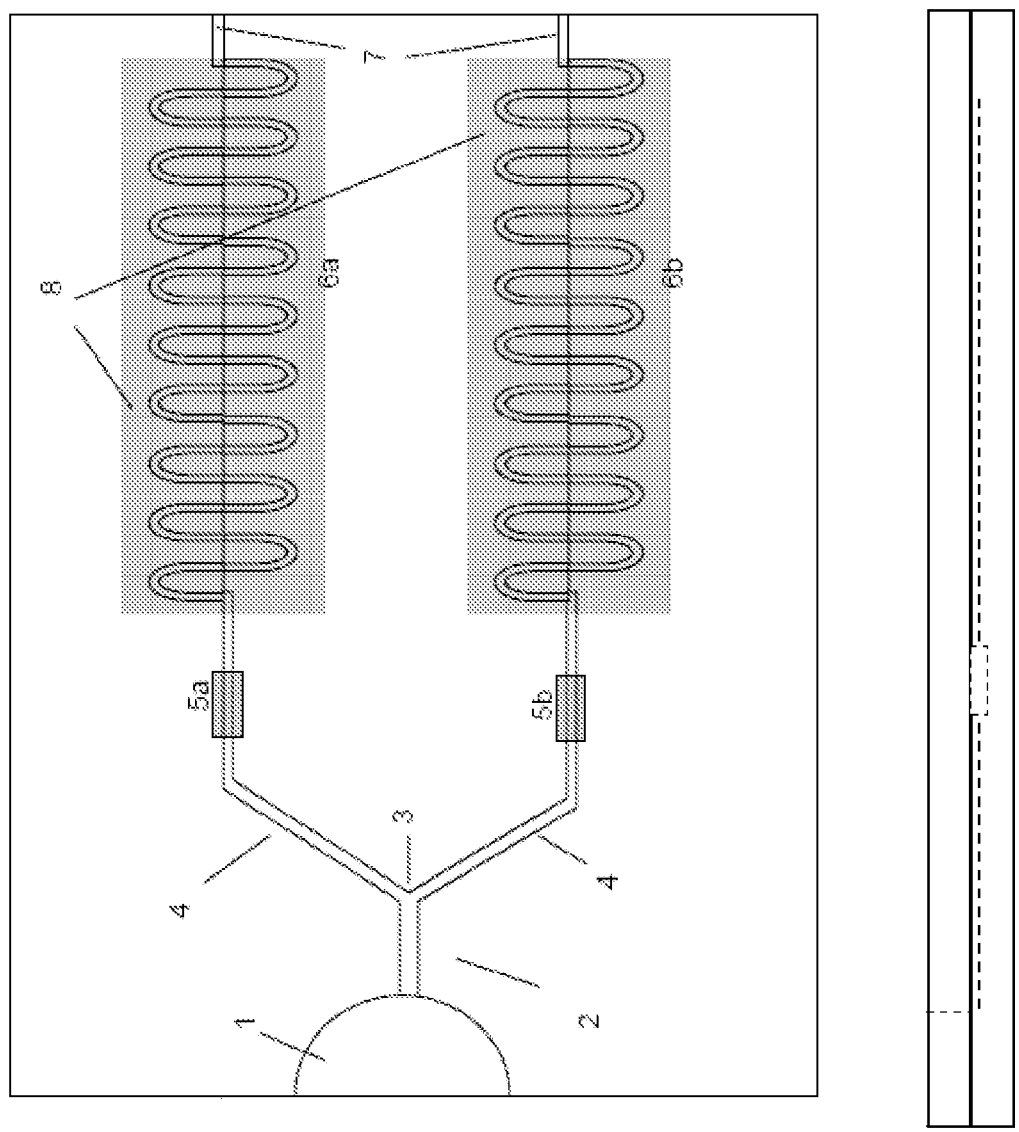
FIG. 2 shows a top view (left part of the figure) and side view (right part of the figure) of the device according to the embodiment of FIG. 1.
Figure 2A:
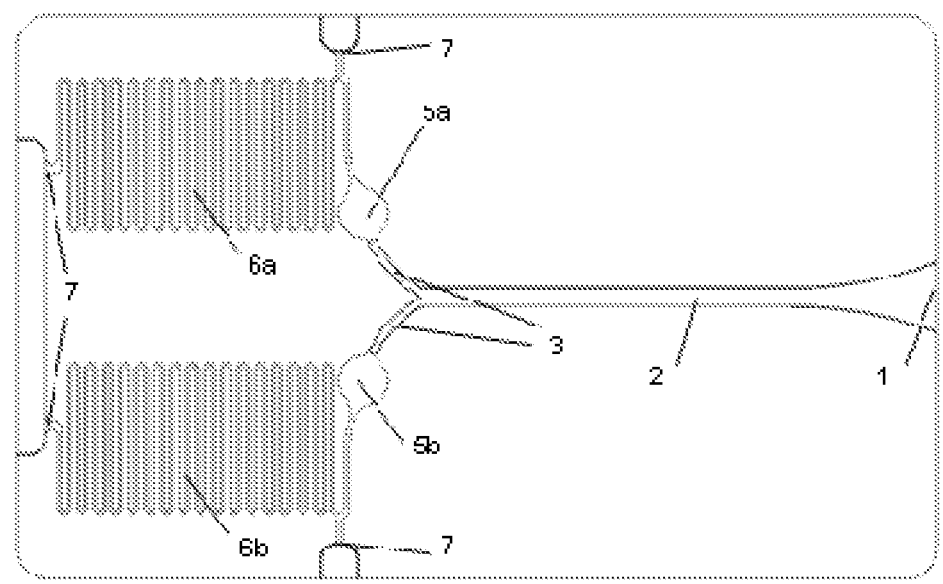
FIG. 2A shows a top view of another embodiment of the microfluidic device.

FIGS. 2 and 2A show a top view of different embodiments of the microfluidic device of the invention, said device comprising the components described below.

Means (1) for introducing a sample of fluid medium, mainly consisting of an inlet port. This inlet port is coupled to a distribution capillary channel (2), followed by a channel bifurcation (3) which splits the distribution channel (2) into a first (6a) and a second region (6b), which permit said fluid medium to flow along a length of said regions. Optionally, the distribution channel contains a cell filter (only depicted in FIG. 1).

In a preferred embodiment, said first (6a) and second (6b) regions have identical structures.

Each of said regions (6a, and 6b) comprise, in order from the distribution channel, first an area (5a, 5b) and at least one microfluidic channel, which will be referred to as the scanning area (8) herein. The first area (5a) contains a first reagent capable of reacting with said fluid medium, and makes the microfluidic channel in region (6a) function as a reaction channel, while the second area (5b) is either empty or contains a different reagent, so that the microfluidic channel in region (6b) functions as a control channel. Preferably, said first reagent is capable of initiating clotting of said fluid medium.

In another embodiment, more than two regions are present in the chip. One of the regions functions as the reaction channel as explained above, and the other two or more are control channels.

For on-board quality control, the blood sample can be capillary driven along control channels where the reaction chambers have specific compounds that provide known and fixed (or narrow band) coagulation times. For example two types of such controls can be incorporated, normalized control and abnormal control, to provide lower and higher references to coagulation times.

The control channels have a different reagent composition from the reagent present in the reaction channel.

Therefore in one embodiment, there is a normalized control channel, the reagent present in it can be for example at least one Vitamin K dependent clotting factor. Such clotting factors can come from a dried or lyophilized pool of normal patient plasmas.

In another embodiment, there is an abnormal control channel, which comprises a clotting factor inhibitor such as, heparines, citrates, oxalates, EDTA and the like. Further, it can comprise the same Vitamin K dependent clotting factors as in the normalized control channel.

The following are illustrative of preferred embodiments describing the number of regions and their functionality:

2 regions: One reaction channel for blood sample clotting time determination with respect to a control channel with no coagulant agent or with a coagulation inhibitor agent.

2 regions: One reaction channel for blood sample clotting time determination through theoretical curves and one control channel which provides normalized clotting times.

3 regions: One reaction channel for blood sample clotting time determination with respect to a control channel with no coagulant agent or with a coagulation inhibitor agent. In addition, another control channel which provides normalized clotting times.

3 regions: One reaction channel for blood sample clotting time determination through theoretical curve comparison. In addition, one control channel which provides normalized clotting times and another control channel which provides known abnormally high clotting times.

All these embodiments and other variants that will be apparent to the skilled person are encompassed by the present invention.

In the device of the invention, the flow is driven by capillary forces only and thus the chip or test strip is a passive device with no needs of external forces. The hydrophilic channel surfaces allow the wetting meniscus to move along the channels towards the negative capillary pressure, while the dewetting meniscus remains at the inlet port. The flow is stopped at stop valves by inducing a hydrophobic surface or by designing a suitable channel opening. In a preferred embodiment, each region (6a, 6b) contains means (7) for venting, most preferably a venting port, which also functions as a stop flow valve. Although depicted at the end of the channel in FIG. 2, the venting ports (7) can be located at other positions along the microfluidic channels. For example, connecting venting ports (7) with flow stops at the exit of the reaction chambers allows that capillary flow speeds up to this point are maximized, as depicted in FIG. 2A. In another embodiments each channel has more than one venting port (7), the venting ports (7) allow to control and modulate the velocity and the flowing properties of the fluid.

At least a property of the fluid medium, preferably the position or the velocity of the fluid front, is monitored as the fluid medium transits scanning areas (8) of the first (6a), second (6b) and optional third regions. Comparison between said properties in said different regions enables detection of the moment when the reaction in the first region (6a) has taken place and the determination of the clotting time for the fluid sample. The regions are preferably capillary channels.

The working principles of this device rely on microfluidics, for which the governing principles radically differ from the conventional flow theory, due to system down-scaling.

Governing Principles

The dynamic filing under Newtonian behaviour of a capillary conduit of constant cross section can be determined through the volumetric flow rate Q, which depends upon the viscosity $\eta$, the total flow resistance $R_{FR}$, and the pressure difference $\Delta P$, between the wetting (front) and dewetting (rear) meniscus:

$$Q = \frac{1}{\eta} \frac{\Delta P}{R_{FR}} \tag{1}$$

For a channel of length "L" and rectangular cross-section A, width "a" and depth "b", the flow resistance $R_{FR}$ can be expressed as:

$$R_{FR} = \left[ \frac{1}{12}\left(1 + \frac{5a}{6b}\right)\frac{AR_H^2}{L} \right]^{-1} \tag{2}$$

Where "$R_H$" is the hydraulic radius and is defined as $$R_H = \frac{ab}{2(a+b)}.$$

To determine L=L(t), i.e. the flow front position against time, the integration of equation (1) with time is required. Thus, L and the velocity, calculated as the derivative of L with time, are expressed as:

$$L(t) = \sqrt{\frac{2\Delta P\left(\frac{1}{12}\left(1 + \frac{5a}{6b}\right)\right)R_H^2 t}{\eta}} \tag{3}$$

$$\frac{dL}{dt} = \sqrt{\frac{\Delta P\left(\frac{1}{12}\left(1 + \frac{5a}{6b}\right)\right)R_H^2}{2\eta t}}$$

These are the governing flow equations prior to clotting, as the viscosity has been assumed constant. When clotting is initiated the viscosity is a function of time, with an exponential increase, so that according to equation (1), the flow rate, which is linearly inverse to viscosity, will undergo a sudden decrease. The curves L(t) and the derivatives shown in further sections have been numerically determined for variable viscosity.

With equations (1) to (3) it is possible to produce a preliminary design of the channel lengths needed to allow permanent flow up to the highest clotting times. The sample volume "V" of a conduit of constant section can be estimated as:

$$V = abL(t) \tag{4}$$

Thus, the device must be designed and the size of the channels chosen according to the existing relation (4) between geometrical parameters of the channels, a, b and L, the volume of sample required and the maximum clotting time.

Clotting Time Determination Through Theoretical Curves

In one embodiment of the invention, taking advantage of the flow dynamics continuous monitoring, the clotting time can be determined or controlled through comparison of the measured property of the sample with the theoretical predicted value.

Since the dynamical behaviour is well predicted prior clotting, the clotting time can be determined as the instant when the monitored clotting curve deviates beyond a particular threshold from the theoretical curves from equations (3). A few mathematical operations can be applied so that such deviation depends only on the qualitative flow dynamic behaviour and not on the quantitative one. Two different but analogous approaches are described as follows:

Method 1:
Step 1:
According to equation (3) for the capillary length under Newtonian behaviour, L(t) is a power function of time. Starting from the L(t) and t values extracted from the detection system, the following curve can be constructed:

$$L(t) = K t^{0.5} \quad (5)$$

Figure 13:
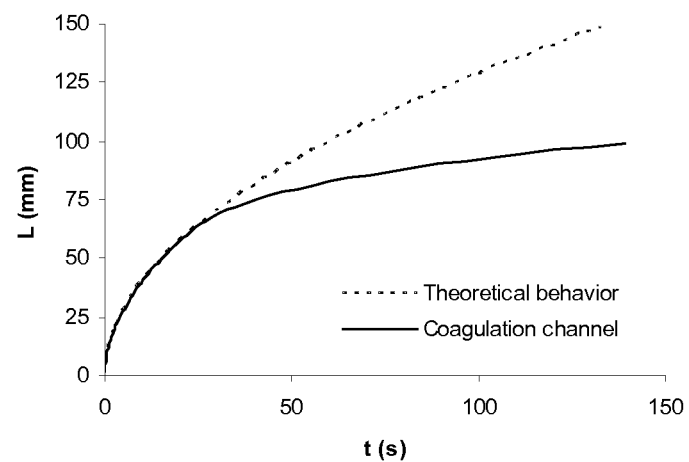
FIGS. 13-16 show graphics of the equations used to determining clotting time through theoretical curves.

The monitored curve (coagulation channel) and theoretical curve are plotted on the graph depicted in FIG. 13.

Figure 14:
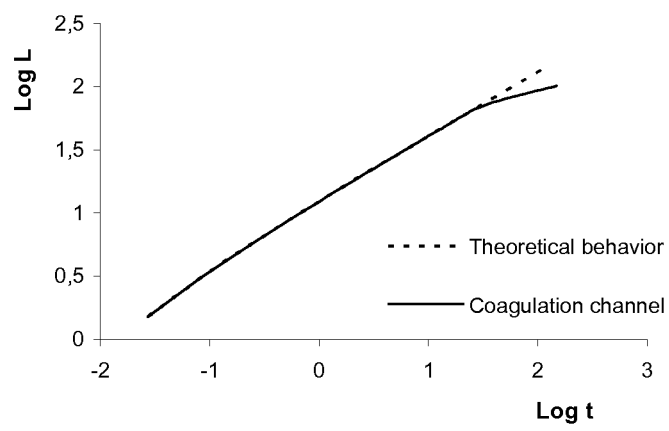

Step 2:
Applying logarithms at both sides of the mentioned expression, a linear curve of 0,5 slope is obtained (see also the graph of FIG. 14):

$$\log L(t) = \log K + 0.5 \log t \quad (6)$$

The quantitative term is log K and the qualitative is 0,5 log t.

Figure 15:
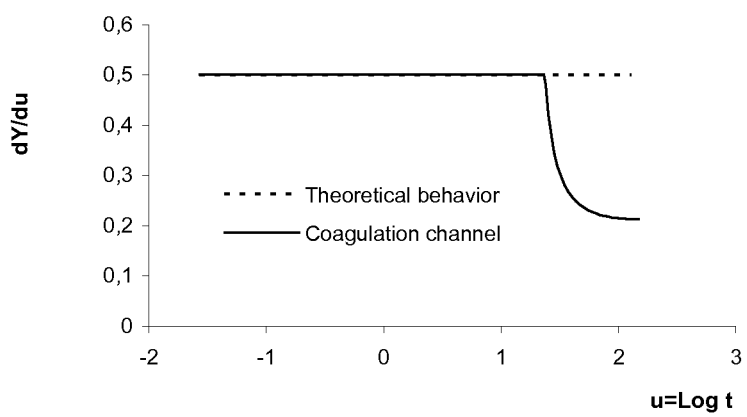

Step 3:
By changing the variable (u=log t) a new function Y=Y(u) can be defined, and differentiating it with respect to u (see also the graph of FIG. 15):

$$Y(u) = \log K + 0.5 u \quad (7)$$

$$\frac{dY}{du} = 0.5 \quad (8)$$

Figure 16:
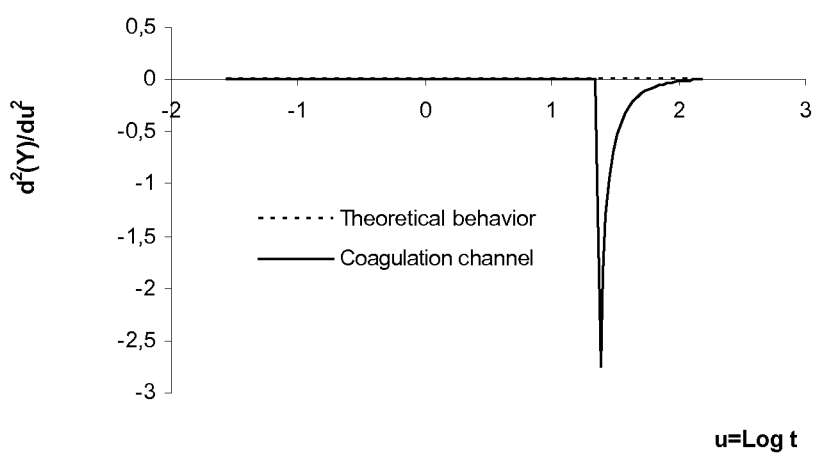

Step 4:
Second differentiation of Y with respect to u is carried out (FIG. 16):

$$\frac{d^2 Y}{du^2} = 0 \quad (9)$$

The decay from the constant value beyond a predefined threshold in either the velocity $$\left(\frac{dY}{du}\right)$$

or acceleration $$\left(\frac{d^2 Y}{du^2}\right)$$

curves determines the clotting time. The above mentioned operations are the mathematical basis of an algorithm that allows the clotting time determination through only one independent coagulation channel.

The microfluidic chip of the present invention is designed so that flowing blood has a predominant Newtonian behaviour prior clotting. Deviation from this behaviour is only due to the pseudo-plastic effect, which can appear at low flow rates. If this occurs, the method still applies and works reasonably well because such pseudo-plastic effect is much weaker than the clotting effect, and can be distinguished on the acceleration curves.

Method 2:
A second and analogous mathematical approach for theoretical clotting time determination can be briefly described as follows. Starting from the same raw data, the L(t) and t values obtained at step 1, the following curve can be constructed:

$$\eta \alpha \frac{L^2}{t} \quad (10)$$

This curve is proportional to viscosity ($\eta$), as can be derived from equation (3). The following steps (2, 3 and 4) are applied identically as before (i.e. logarithm application, first derivative and second derivative), so that velocity and acceleration curves are constructed.

Figure 17:
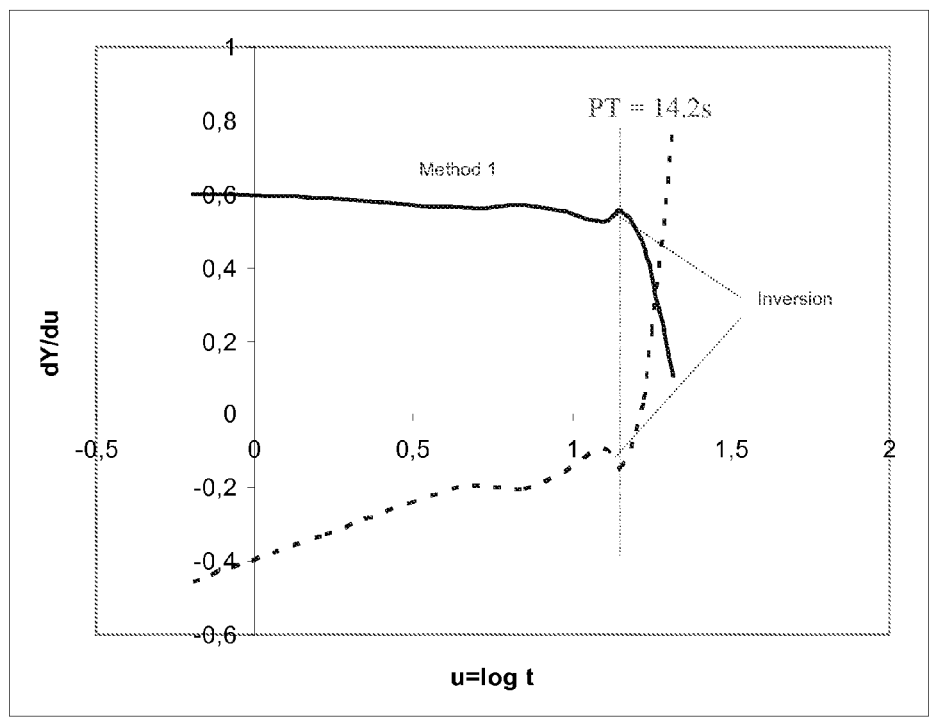
FIG. 17 shows typical data at step 3 from real coagulation tests and clotting times as determined following theoretical method 1 or 2.

Based on real test data, both methods roughly give the same clotting time (PT). A surprising result found in practically all monitored curves, as the ones shown in the graph of FIG. 17, was an initially unexpected behaviour which is opposed to the coagulation effect, see the highlighted areas in both curves under the term "inversion". This effect is in fact a transient viscosity decrease of about 1 or 2 seconds duration which is always seen just prior the clotting time. This behaviour provides an easier clotting time identification as the PT instant thus becomes a clear inflection point, either a maximum in method 1 or a minimum in method 2. Although the reason for this unexpected behaviour is unknown, some evidence suggests that this can be due to the formation of the fibrin insoluble monomers coupled with the Fahraeus-Lindqvist effect, which reduces the apparent viscosity prior to the formation of fibrin polymers.

Besides the clotting time determination, the theoretical approach described above, can also be employed for quality control by correlating the test curves with the theoretical predictions. Under a normal operator (i.e. no patient misuse) and correct device conditions, the blood sample flow prior to clotting should lie close to the mentioned linear behaviour. Any significant deviation from such behaviour can be detected and processed by the flow monitoring system and processor, providing a test cancellation order.

According to a preferred embodiment the fluid medium is blood, preferably capillary whole blood from patient fingerpricking, and calibrated plasma with known clotting times can be used for external quality control. The reagent capable of reacting with said fluid medium is a clotting reagent, more preferably a tissue factor or thromboplastin.

In this case, the device and method of the invention are particularly suited to determine the Prothrombin Time, i.e. the time elapsed between clotting activation and start of clotting.

The device can be designed according to standard INR values; the recommended highest INR range is about 8, which also means PT about 100 seconds. The dimensions required for reaching such a maximum INR are shown in Table 1. As previously mentioned, the required dimensions and total volumes "$V_t$" of different conduits designs are governed by equation (3).

TABLE 1

Required lengths and total volumes "Vt" of different conduits designs for reaching such maximum INR range (100 sec).

| | a (mm) | b (mm) | L (mm) | $V_t$ (μL) |
|---|---|---|---|---|
| Microfluidic design | 0.08 | 0.08 | 150 | 1.0 |
| Microfluidic design | 0.125 | 0.125 | 250 | 3.9 |
| Intermediate design | 0.5 | 0.5 | 500 | 125 |
| Conventional design | 1 | 1 | 700 | 700 |

This table demonstrates that simply, by downscaling the fluidic design to the microscale, the standard INR range can be achieved with just a blood droplet.

The shape and the dimensions of the channels according to the present invention allow the determination of the clotting time of a blood sample of no more than 15 μl, and the total volume allocated when all the circuits are filled is less than 10 μl allowing a remaining volume within the inlet port, necessary to fix the dewetting meniscus at the inlet port. The microfluidic channels allow a continuous flow, lasting from several seconds to more than a hundred seconds, allowing the PT determination around a long time range. Thus the chip and method of the invention allow the measurement of accurate clotting times and INR determination with low amounts of blood sample, preferably below 10 μl, more preferably below 5 μl, and most preferably with about 1 μl or less. This is very important for the convenience of the patient.

The length of the capillary channels (6a, 6b) should be large enough to enable the reaction of the reagent with the fluid to be completed before the fluid front reaches the end of the channel. In a preferred embodiment the capillary channels (6a, 6b) are in a curved shape, most preferably having a serpentine shaped track, in order to minimize the area of the device while maintaining the length of the channels.

The preferred cross-section of the channels is rectangular due to manufacturing constrains, allowing a pure 2D geometry, which simplifies the mould fabrication processes. The specific dimensions have to be carefully calculated as the flow dynamic, and total volume employed is very sensitive to channel dimensions. As shown herein, dimension values well above 100 μm require very large channel lengths to permit flow durations up to the highest clotting times, and higher blood sample volumes are required. With a microfluidic design, or in other words, channel cross section dimensions about 100 μm or less, channel lengths can be reduced with little blood usage. In addition the size of the chip and its cost are also reduced considerably.

Preferably, the reaction and control channels have a cross-section where a=b. In this case a and b are preferably between 30 to 125 μm, more preferably between 50 and 100 μm, and even more preferably of about 80 μm.

Also the dimensions of the area containing the reagent, preferably a reaction cell, must be appropriate to allow enough volume for dispensing the reagent in liquid state. Besides, the design has to be defined so the diffusion time permits reaching enough reagent concentration in order to maximize the activated blood volume. This can be achieved by maximizing the surface to volume ratio within the reaction chamber. Preferably, the footprint chamber design should be circular for adapting to droplet dispensed shape, with dimensions between 1 to 4 mm in diameter and height between 40 to 150 μm. More preferably, the diameter is about 1.5 mm and height is about 80 μm.

The height dimension of the distribution channel is preferably between 150 μm and 350 μm, more preferably about 250 μm.

The blood inlet port is preferably the gap left between the cover and base substrates at the edge of the chip, on the distribution channel, and therefore can have the height of said distribution channel. Volume allocated on the distribution channel should be slightly larger than the volume allocated in the subsequent capillary structure, so that once the distribution channel is completely filled with fluid it can never be emptied. This volume defines the minimum test sample volume requirement.

In order to fulfil construction requirements and dimensional constrains, the flow rate Q can be modified through the introduction of passive flow control valves by modifying the cross section of the microfluidic channels, for example, by narrowing segments of the microfluidic channels or by introducing tapered microfluidic channels.

Operation of the Microfluidic Device

The present invention requires applying a sample of blood or plasma to the inlet port, through which the blood or plasma enters the sample distribution channel, along which the same blood sample or plasma is split into a reaction/clotting channel and one or more control channels.

At a time $t_m$ prior to blood clotting the flow front positions in the channels can be represented as follows, $$L = L(tm)$$

$$L' = L'(tm) \quad (11)$$

Where L y L' are respectively the clotting and control positions. The time t=0 is the instant the flow exits the reaction cell of the clotting channel, as it is the moment the tissue factor or thromboplastin has solubilized and the reaction mechanisms are initiated.

The split flows have nearly identical motion dynamics until the coagulation is initiated in the clotting channel. This instant, when the first blood clotting occurs, is identified as the Prothrombin Time, and induces a sudden increase in viscosity. At this instant the flow dynamics along the clotting channel is decelerated with respect to the control channel(s). By continuous monitoring (8) the flow front position as a function of time, the derivative of the position with time, which can be referred to as the flow front velocity, can be calculated.

Figure 3:
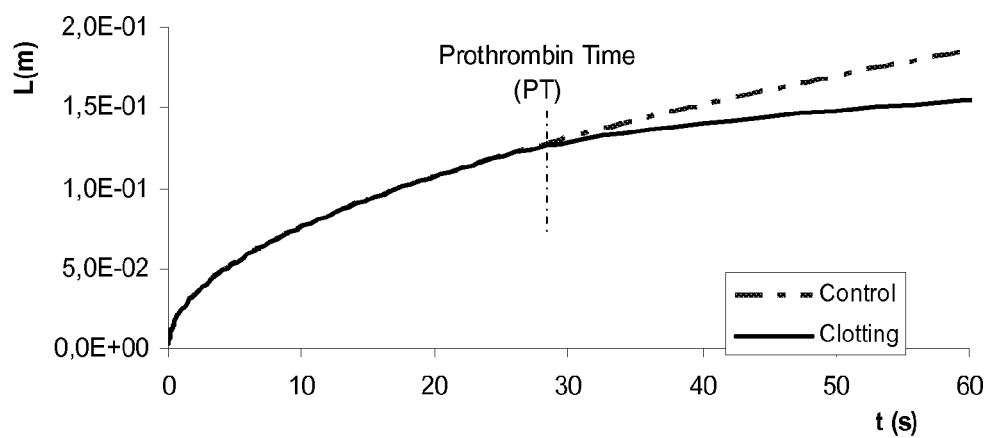
FIG. 3 shows a graphical representation of the superposition of the flow front positions in the clotting and control channels.

In FIG. 3, it is illustrated how the flow front positions in two channels and the Prothombin Time can be identified. These curves have been numerically calculated with the following assumptions, where variables a, b, η and PT have the meaning indicated previously herein, and γ is the blood surface tension:

TABLE 2

Assumptions for the numerical calculations.

| γ (N/m) | 0.05589 | Contact angle | 35 |
|---|---|---|---|
| a (m) | 0.000125 | η (Pa s) | 0.0003 |
| b (m) | 0.000125 | PT | 25s |

Prior to PT the difference between the channels should be minimal, only affected by non-uniform environmental conditions, manufacturing tolerances and detection noise. The derivative with time curves are preferred as it is a more sensitive to viscosity changes, which can be referred as the flow front velocities. Analogously at a time $t_m$ prior to PT, the velocities are monitored for clotting (V) and control (V') will be:

$$V = V(t_m)$$

$$V' = V'(t_m) \tag{12}$$

Figure 4:
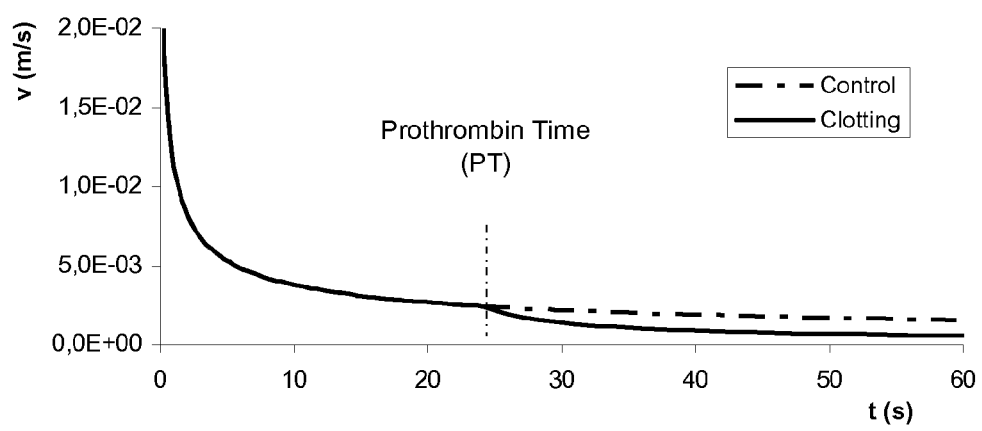
FIG. 4 shows a graphical representation of the superposition of the flow front velocities in the clotting and control channels.

These curves are shown in FIG. 4.

Figure 5:
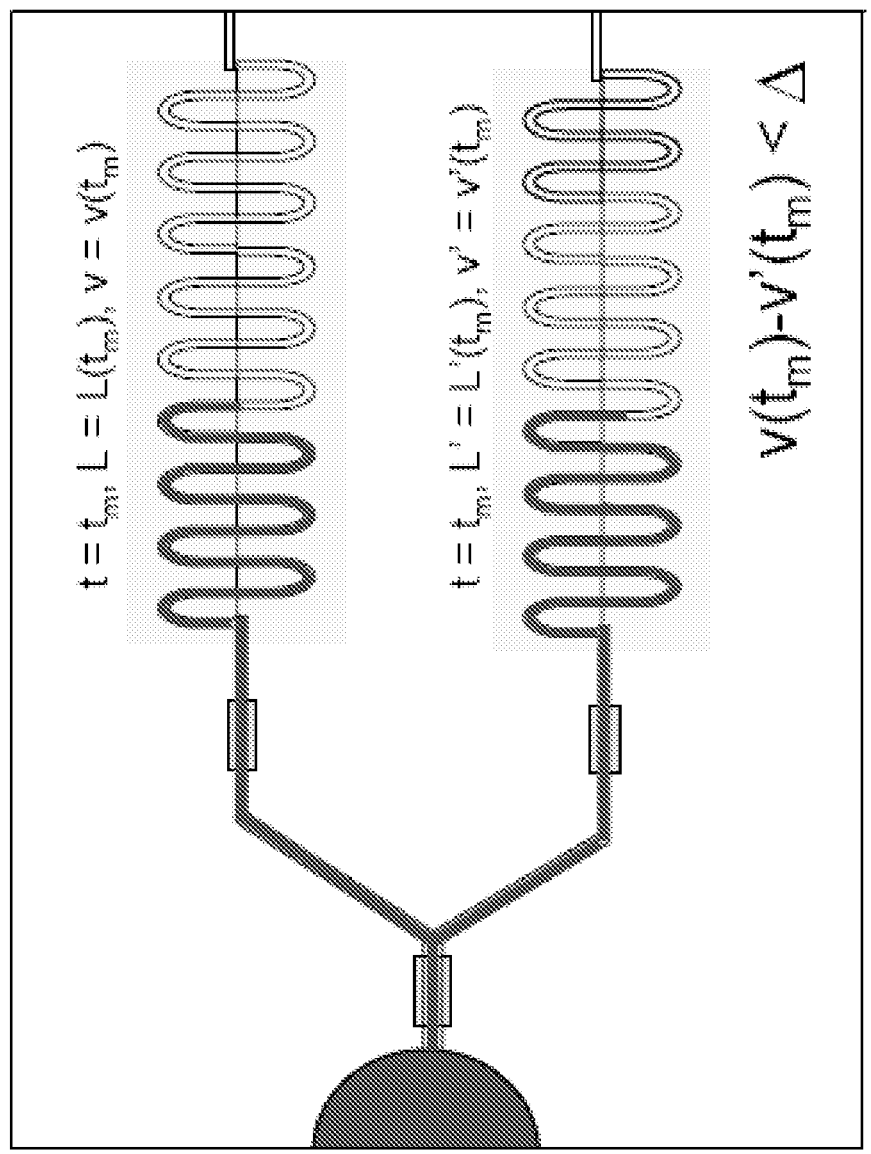
FIG. 5 shows the schematic flow front positions prior to clotting in the embodiment according to FIG. 1.

PT can be determined by defining a suitable threshold "Δ" for the difference between the velocities $V(t_m)-V'(t_m)$. Prior to PT, the viscosity is constant and the flow front positions and velocities have minor differences as schematically shown in FIG. 5.

Figure 6:
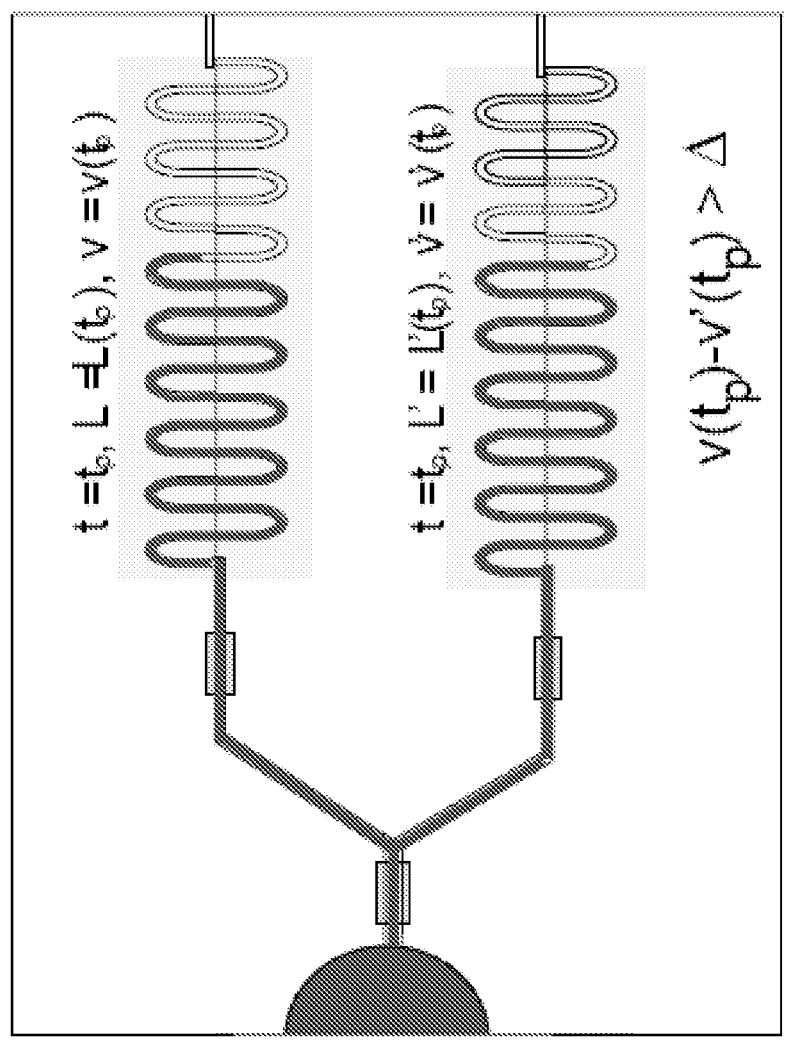
FIG. 6 shows the schematic flow front positions after clotting in the embodiment according to FIG. 1.

At a time $t_p$ the velocity difference has just surpassed the threshold (see FIG. 6) and this instant is PT.

Detecting Means

For a continuous detection or monitoring of the flow front motion $L=L(t)$ or $v=v(t)$ different detection techniques can be used:

Detection through Photodiode

Detection through optical sensors such as Charged-Coupled-Device (CCD) or Complementary Metal Oxide Semiconductor (CMOS).

Figure 7:
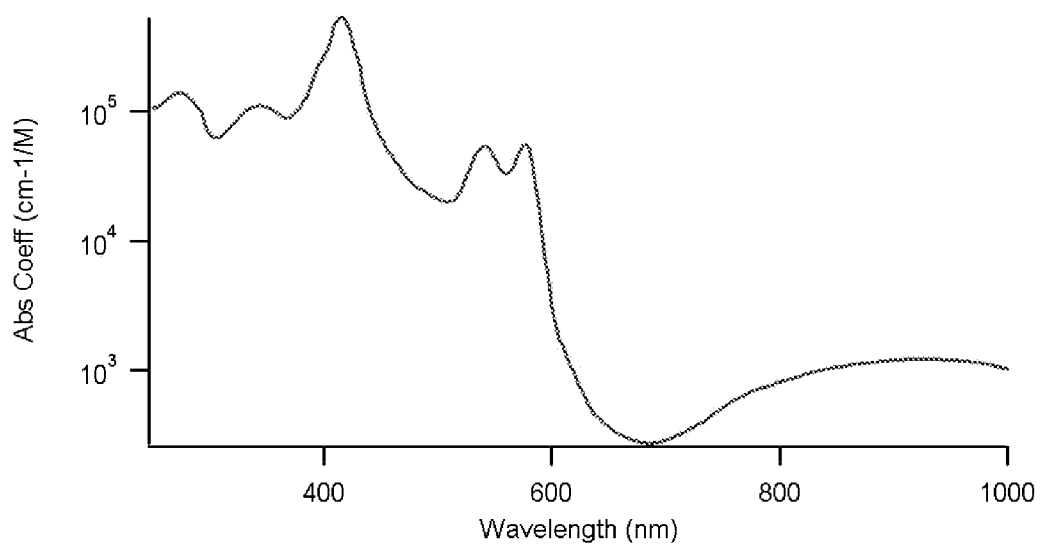
FIG. 7 shows the absorption coefficient of blood vs. wavelength.

The coefficient of absorption of blood is plotted in FIG. 7. It can be seen that it absorbs especially at 400 nm, and also around the green (530 nm).

Detection Through Photodiode

The serpentine is illuminated with a LED and transmitted light is detected with the photodiode. The moving flow front linearly increases the absorption and thus the intensity detected is accordingly reduced. With a signal amplifier it is possible to monitor tiny flow position increments.

In the following some calculations have been carried out to evaluate the viability of such monitoring scheme, using standard low cost components.

A LED and a photodiode, both low cost, from readily available distributors have been selected.

The LED has 3 mm size and emits within a 20° angle. The intensity is 15000 mcd=0.0309 Watts/str, so by taking the whole 20° solid angle (0.095 str) the total emission power reaches 0.00294.

Figure 8:
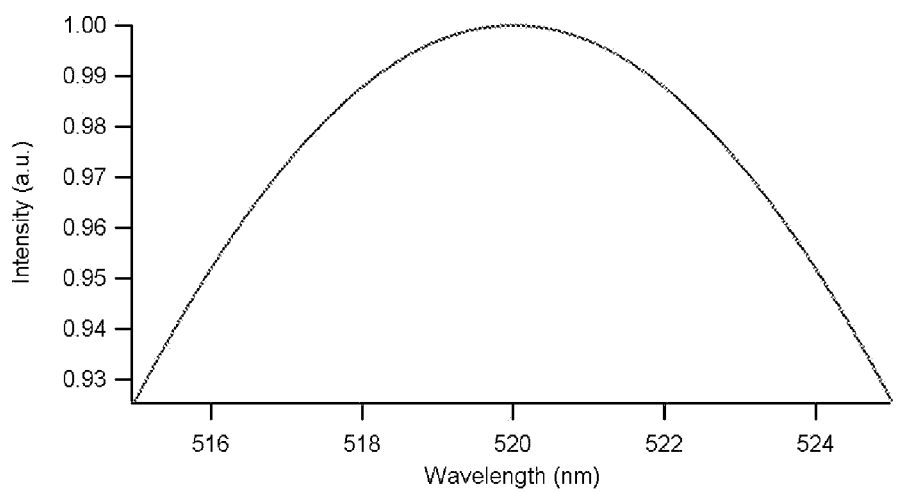
FIG. 8 shows the emission spectrum of a LED.
Figure 9:
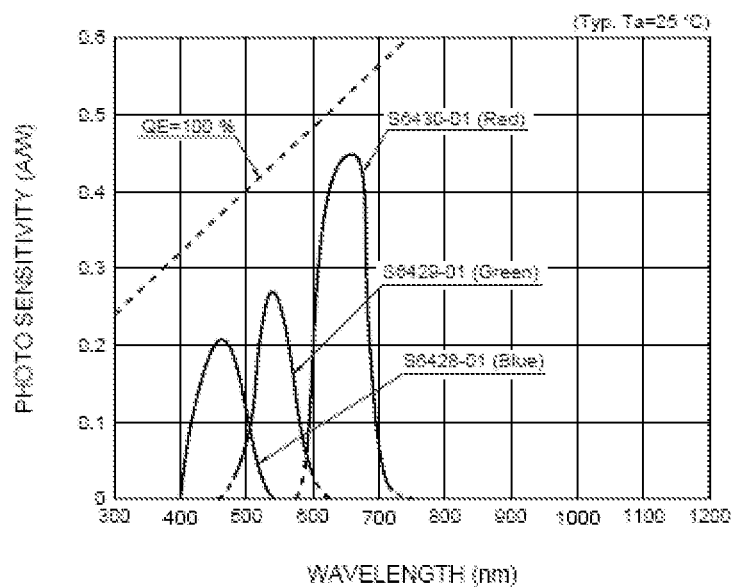
FIG. 9 shows the response curve of a photodiode optimized to detect the greenish wavelengths.

The emission spectrum of the LED and the response curve of the photodiode, which is a standard Silicon one but also optimized to detect the greenish wavelengths, can be shown in FIGS. 8 and 9.

Figure 10:
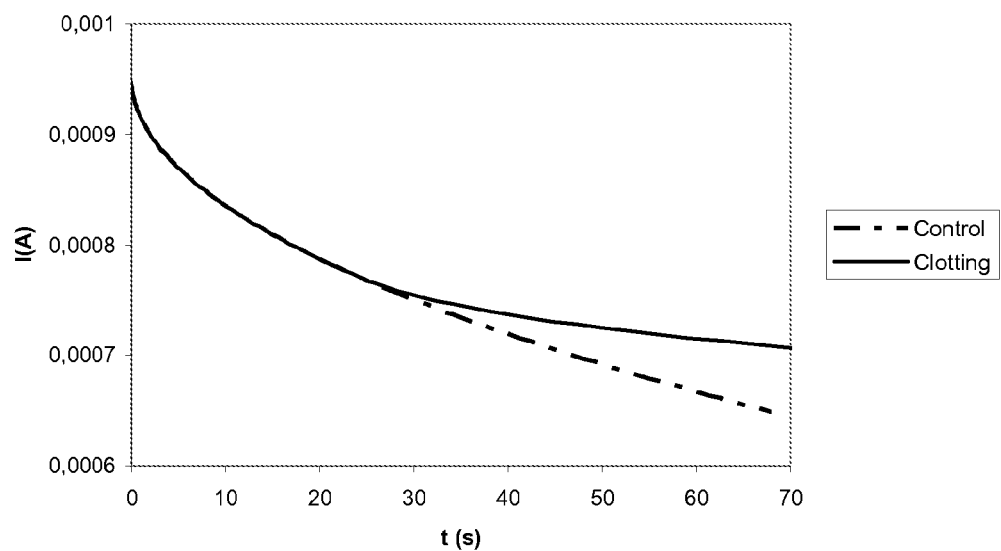
FIG. 10 shows the detected current intensity versus time in two chips of different size for the clotting and control channels.
Figure 11:
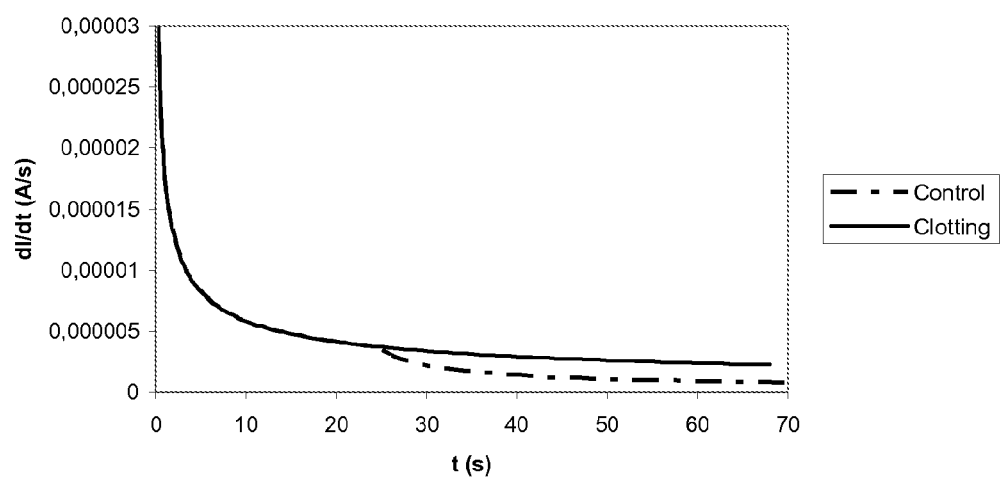
FIG. 11 shows the derivatives of the current intensity curves of FIG. 10.

Under these assumptions and by further acquiring the scanning area (8), channel dimensions and the actual L(t) curve from FIG. 3, the intensity signal detected by the photodiode can be obtained. For simplicity reasons, it has been also assumed that the chip is perfectly transparent and no Fresnel reflections are taking place. The Intensity signal, plotted in FIG. 10, also contains a dark current random noise simulation of 20 picoA, as specified by the manufacturer. This curve corresponds to a channel section of 250×250 µm. By calculating the derivative of the intensity signal with time, a signal proportional to the flow velocity can be obtained, as shown in FIG. 11.

With the two shown plots (FIGS. 10 and 11) it is demonstrated that the flow front monitoring is viable, with a sufficiently high sensitivity, as can be deduced from the negligible noise affecting the curves. In addition, the time response of the photodiode is very high, which permits frequency sampling as high as 10 MHz and the amplifier itself is limited to 10 Khz. This values are orders of magnitude beyond the needed frequency for accurate monitoring, about 20 Hz.

Detection Through Optical Sensors

With this detection scheme, the system employs a similar configuration but substituting the detection device. In this case we employ CCD or CMOS sensors, so that flow front position is obtained by processing the data acquired after high frequency mapping of the scanning surface.

Figure 12:
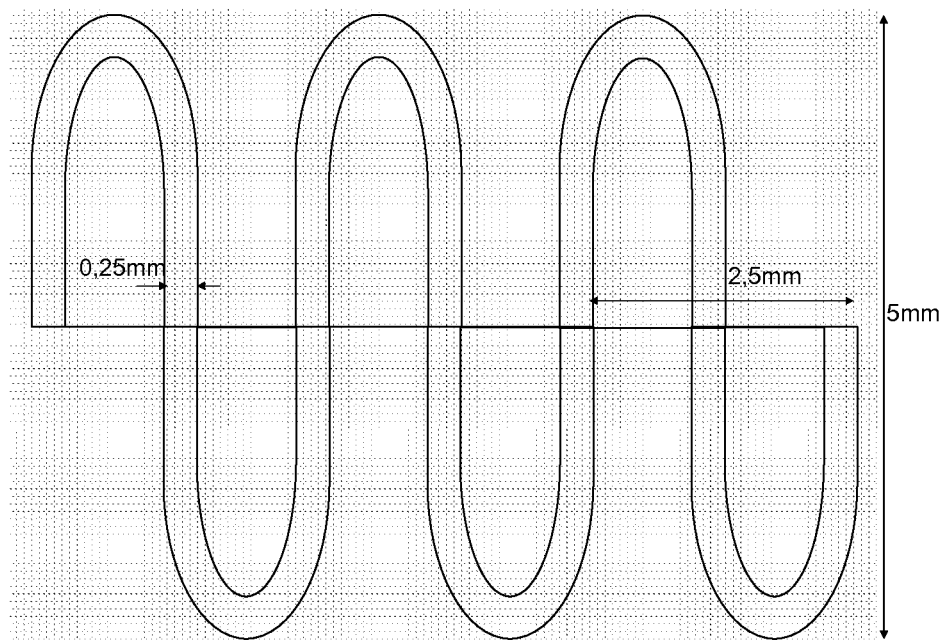
FIG. 12 shows the superposition of a serpentine of the embodiment according to FIG. 1 and a CCD array with pixel sizes 19×19 µm.

The LED system can be similar to the one defined in the previous case. Interestingly, in this case no high sensitivity is required, as each cell or pixel within the CCD is to detect the presence of absence of flow in this position. As shown in FIG. 12, by superposing the CCD effective area of a standard with the serpentine, the mapped image would allow the identification of the flow front position, with enough resolution and time response (>1 KHz).

This technique requires image data processing, so that from a blurry image the meniscus position can be identified. This increases the complexity of the monitoring system. However, and in contrast with the photodiode detection scheme, the sensitivity of each cell or pixel is less stringent, which in this sense will favour the CCD detection scheme.

In order to improve the detecting signal quality, optical means, such as a lens can be integrated. Commercial rigid blocks, integrating lens and sensor are available nowadays at very low cost, such as the miniature cameras that are supplied to the mobile industry. These blocks measure just a few millimetres and thus allows very compact and thin integration into portable systems, such as the portable coagulometer.

The detected signal is processed by the microprocessor with embedded software. Dynamic flow data curves are generated and the algorithms are employed for coagulation time determination and also for various quality controls.

As explained before, the chip (test strip) and method of the invention have another significant advantage, in that the same detection means can be used for monitoring the sample fluid flow and for fulfilling various quality control task.

When the detection means is provided through artificial vision system, such as CCD/CMOS sensor or microcamera, three main quality controls, usual in test strips for coagulameters, can be performed through field of view image processing of such a vision system:

On-board ambient condition indicators for stability monitoring: ambient conditions such as temperature and humidity can be monitored through colour sensitive compounds to these factors. The selected compounds undergo an irreversible colour change when subjected to temperature and humidity thresholds, signalling a deficient chip. They can be added directly on the reaction chambers, on the base substrate or on the cover surface, under the detector's field of view. A combination of different sensitive compounds can be used to this end. Examples of such compounds as sensible temperature compounds: Leuco dyes, Oxazines, Crystal violet lactone, phenolphthalein and the like. Metallic salts as sensible moisture compounds: cobalt chloride, calcium sulfate and the like. N-oxide or Nitroso compounds as both temperature and moisture sensible compounds.

This will allow the measuring device (such as portable coagulometer) to inform the patient that the test strip has not passed the quality control and should be discarded.

External quality control: calibrated plasmas with known clotting times, commercially available for performing INR and PT test calibrations, can be used as external quality control, so that the whole portable coagulometer system can be evaluated. In this embodiments the artificial vision system is adjusted to allow detection of the flowing plasmas. Although plasma is a nearly transparent fluid, little adjustment of the illumination led system and image processing is required to effectively track plasma flow, since moving plasma is recognized like a grey shadow advancing along bright channels.

Printed Codebar: printed code carrying among other relevant information calibration data, traceability data and expiry date. Standard data matrix codes of a few millimeters dimensions used in this kind of test strips can be printed onto the chip's cover layer or onto a transparent label.

The suitable detecting and/or monitoring means described above are comprised in an external device (coagulometer) which comprises a slot for receiving the microfluidic device of the invention and is designed to cooperate with said microfluidic device.

Additionally, the external device comprises means for processing the data delivered by the detecting and/or monitoring means and produces a signal output into a displaying means.

Manufacturing

The present microfluidic device can be easily manufactured with current plastic replication technologies and assembling techniques. The assembly is formed by two sealed components: the lower substrate, where the microstructures are patterned and the top substrate or cover lid, as illustrated in FIG. 1.

The materials suitable for both the lower substrate and the cover layer of the device are a range of polymer, thermoset and/or thermoplastic materials should have good optical properties and good dimensional stability. For example, COC, PMMA, PC, PSU, SAN, PETG, PS and PP can be used.

Most polymeric materials are hydrophobic in nature. Therefore if a strongly hydrophobic material is chosen as patterned substrate, a subsequent production step to render hydrophilic some surfaces would be necessary, as explained before. For this reason, hydrophilic or at least not hydrophobic (contact angle <90°) plastics are recommended.

That is the case for PMMA, Cellusose Acetate, PC, COC and PS, among other well known materials. One material that is particularly preferred is PMMA, in view of its good contact angle, optical properties and dimensional stability.

The lower substrate can be easily replicated with a range of technologies, available today, and with very high accuracies, allowing low microfeature tolerances. The most relevant current techniques for said patterning step are microinjection moulding, hot embossing and soft lithography imprinting.

The sealing step can be performed with a number of well known techniques such as thermal compression bonding, adhesive bonding, plasma activated bonding, ultrasonic bonding, laser welding and others.

The cover is preferably a hydrophilic film. It is preferably transparent, to allow accurate monitoring of the fluid flow. As explained above hydrophilic films provide very cost-effective means that enable both sealing and channel hydrophilization, avoiding the surface treatment step. In this case, the production technique consists of standard lamination processes, which can require pressure and temperature control. Other production techniques are embossing or pressing processes.

As described above the Reaction chambers can allocate a number of dry-reagent compounds for various purposes. The main compound is thromboplastin to initiate the coagulation cascade. Due to the tiny dimensions of the reaction chamber high performance compounds can be added without significantly increasing the cost of production.

Human thromboplastin recombinants have extremely useful properties in terms of solubilization and sensitivity due to their chemical purity. The former property has been traditionally enhanced by the use of specific additives. Under the present invention's design, a fraction of a microliter of human recombinant factor can be dispensed, showing excellent results in terms of solubilization and sensitivity.

A number of additional agents play a role in the proper functioning of the dry reagent. They may be employed not only for rapid solubilization, but also for control diffusion parameters, improving fabrication steps and reagent stability, or for addressing the following issues:

a) Modulate uptake of the liquid into the dry reagent: simple polymers such as hydroxylpropyl cellulose, polyvinyl alcohol, polyethylene glycol and the like.
b) Rapid solubilization, stabilizers and shortening the drying process: albumin, glutamate, sacarides, (such as glucose, saccharose, trehalose, etc), and the like.
c) Controlled wettability: Triton, Macol, Tetronic, Silwet, Zonyl, Pluronic, and the like.
d) Color indicator for monitoring stability and for dispensing control: Leuco dyes as sensible temperature compounds (Oxazines, Crystal violet lactone, phenolphthalein and the like.). Metallic salts as sensible moisture compounds such as cobalt chloride, calcium sulfate and the like. N-oxide or Nitroso compounds as both temperature and moisture sensible compounds.
e) Enhancing ambient conditions stability: organomercury compounds such as Thimerosal and the like.
f) Other compounds for various functionalities: Polybrene (antiheparin agent) and buffers.

The dry-reagents can be applied on the reaction chamber or alternatively onto the cover substrate, through a number of well known techniques: liquid drop dispensing, gel dispensing, jet dispensing, screen printing, blade coating, selective spraying and film casting. The dispensing step is followed by a drying step.

Preferably, dry reagent is dispensed in liquid state onto the reaction chamber forming a droplet occupying most of the chamber that upon drying becomes a thin dry-reagent layer.

Advantageously, both the manufacturing method and the chip (test strip) so fabricated are extremely simple, no embedded components are required, such as electrodes or any form of multilayer structures. Indeed, the presented manufacturing techniques allow low cost production, so that cheap disposable devices can be produced.

The current invention, through its microfluidic design, provides very sensitive and accurate means for clotting time determination. The clotting time (such as the Prothrombin Time) relates to the moment when the insoluble fibrin molecules start to polymerise that later produces a "mesh" that forms the clot. The formation of fibrin polymers, typically of the order of a few micrometers, leads to an abrupt increase on the apparent viscosity of the flowing blood, specially when the channel cross-section becomes as tiny as in the current microfluidic design. In terms of accuracy and sensitivity, this device offers the previously mentioned advantages with respect to previous devices for clotting time determination.

In addition, the combination of chip and measuring device of the invention provides combined advantages. The use of single optical detection means allows to simultaneously combine the detection of fluid flow changes and different quality controls. This means that the portable measuring device will be less complex and more compact, using standard components. In fact the measuring device can have the size of a mobile telephone. There is also a significant improvement in precision and sensitivity from previous devices, especially those that are based upon blood flow, as the flow monitoring is made continuously with a high frequency sampling. In this way, the very instant when the clot formation has the first decelerating effect on blood flow can be accurately determined.

As will be recognised by those skilled in the art, the innovative concepts described in the present application can be modified and varied over a wide range of applications.

The invention claimed is:

1. A microfluidic device for determining clotting time in a fluid medium, said device comprising:
    an inlet for introducing a sample of said fluid medium comprising an inlet port coupled to a distribution capillary channel, followed by a bifurcation channel which splits the distribution capillary channel into a first and a second region, wherein the fluid medium comprises blood or plasma;
    wherein the first region is coupled with said distribution capillary channel for permitting said fluid medium to flow along a length of said first region, the first region comprising in order from the distribution channel:
    a first area at the beginning of said first region, containing a first reagent capable of reacting with said fluid medium, and at least one microfluidic channel which is the scanning area of the first region;
    wherein the second region is also coupled with said distribution capillary channel for permitting said fluid medium to flow along a length of said second region, the second region comprising in order from the distribution channel: a second area at the beginning of said second region and at least one microfluidic channel which is the scanning area of the second region, wherein said second area does not contain a reagent capable of reacting with said fluid medium or contains a second reagent capable of reacting with said fluid medium which is different from the first reagent of the first area;
    wherein the microfluidic channels of the first and second region comprise a serpentine shaped track to minimize the area of the device while maintaining the length of the channels, and wherein the first and second areas have a higher surface to volume ratio than the bifurcation channel or the microfluidic channels, and
    wherein said first region and second region are capillary channels having capillary channel surfaces, wherein the capillary channel surfaces of said capillary channels are hydrophilic and capillarity acts as the only force for moving the fluid medium, and wherein each of said first region and said second region comprises a vent.

2. The microfluidic device according to claim 1, said vent comprising a venting port functioning as a stop flow valve.

3. The microfluidic device according to claim 1 characterized in that said first area of said first region comprises a reaction cell containing a first reagent capable of initiating clotting of said fluid medium.

4. The microfluidic device according to claim 1, further comprising a third region, also coupled with said distribution capillary channel, for permitting said fluid medium to flow along a length of said third region, wherein at the beginning of said third region there is a third area containing a third reagent capable of reacting with said fluid medium which is different than the first reagent of the first area or the second reagent of the second area, and wherein said first region and said second region comprise a serpentine shaped track to minimize the area of the device while maintaining the length of the channels.

5. The microfluidic device according to claim 4 characterized in that said first region acts as a clotting channel and said second region and said third region act as control channels, and in that each of said first region, said second region, and said third region has identical structure.

6. The microfluidic device according to claim 1 characterized in that at least one of said first region and said second region has a rectangular cross section microfluidic channel.

7. The microfluidic device according to claim 1 characterized in that at least one of said first region and said second region has a channel formed of a combination of segments of different cross-sections.

8. The microfluidic device according to claim 1 characterized in that said first reagent in said first area is thromboplastin and said clotting time represents prothrombin time.

9. The microfluidic device according to claim 1 characterized in that said first region acts as a clotting channel and said second region acts as a control channel and in that each of the two regions have identical structure.

10. The microfluidic device according to claim 1 further comprising an optical feature for quality control.

11. A method for determining clotting time in a fluid medium such as blood or plasma comprising:
    introducing a sample of said fluid medium to a microfluidic device, said microfluidic device comprising:
        an inlet for introducing a sample of said fluid medium comprising an inlet port coupled to a distribution capillary channel, followed by a bifurcation channel which splits the distribution capillary channel into a first and a second region, wherein the fluid medium comprises blood or plasma;
        wherein the first region is coupled with said distribution capillary channel for permitting said fluid medium to flow along a length of said first region, the first region comprising in order from the distribution channel:
        a first area at the beginning of said first region, containing a first reagent capable of reacting with said fluid medium, and at least one microfluidic channel which is the scanning area of the first region;
        wherein the second region is also coupled with said distribution capillary channel for permitting said fluid medium to flow along a length of said second region, the second region comprising in order from the distribution channel: a second area at the beginning of said second region and at least one microfluidic channel which is the scanning area of the second region, wherein said second area does not contain a reagent capable of reacting with said fluid medium or contains a second reagent capable of reacting with said fluid medium which is different from the first reagent of the first area;
        wherein the microfluidic channels of the first and second region comprise a serpentine shaped track to minimize the area of the device while maintaining the length of the channels, and wherein the first and second areas have a higher surface to volume ratio than the bifurcation channel or the microfluidic channels, and
        wherein said first region and second region are capillary channels having capillary channel surfaces, wherein the capillary channel surfaces of said capillary channels are hydrophilic and capillarity acts as the only force for moving the fluid medium, and wherein each of said first region and said second region comprises a vent;
    providing at the beginning of said first region in the first area a first reagent capable of reacting with said fluid medium; and
    providing in said second region in the second area no reagent or a second reagent different from the first reagent in said first region, continuously monitoring with an optical detector at least one property of said fluid medium in said first region and said second region, and comparing the at least one property of said fluid medium in said first region with said second region or against a theoretical value.

12. The method for determining clotting time in a fluid medium such as blood or plasma according to claim 11 characterized in that the comparison of the at least one property of said fluid medium in said first region it is made against at least a property of said fluid medium in said second region.

13. The method for determining clotting time in a fluid medium such as blood or plasma according to claim 11 characterized in that the comparison of the at least one property of said fluid medium in said first region is made against a theoretical value for said property.

14. The method for determining clotting time in a fluid medium such as blood or plasma according to claim 11 further comprising a quality control step of correlating at least one property with a theoretical curve.

15. A method of manufacturing a microfluidic device for determining clotting time in a fluid medium such as blood or plasma comprising:

providing a first substrate;

patterning in said first substrate a microstructure corresponding to a microfluidic device, said microfluidic device comprising:

an inlet for introducing a sample of said fluid medium comprising an inlet port coupled to a distribution capillary channel, followed by a bifurcation channel which splits the distribution capillary channel into a first and a second region, wherein the fluid medium comprises blood or plasma;

wherein the first region is coupled with said distribution capillary channel for permitting said fluid medium to flow along a length of said first region, the first region comprising in order from the distribution channel:

a first area at the beginning of said first region, containing a first reagent capable of reacting with said fluid medium, and at least one microfluidic channel which is the scanning area of the first region;

wherein the second region is also coupled with said distribution capillary channel for permitting said fluid medium to flow along a length of said second region, the second region comprising in order from the distribution channel: a second area at the beginning of said second region and at least one microfluidic channel which is the scanning area of the second region, wherein said second area does not contain a reagent capable of reacting with said fluid medium or contains a second reagent capable of reacting with said fluid medium which is different from the first reagent of the first area;

wherein the microfluidic channels of the first and second region comprise a serpentine shaped track to minimize the area of the device while maintaining the length of the channels, and wherein the first and second areas have a higher surface to volume ratio than the bifurcation channel or the microfluidic channels, and wherein said first region and second region are capillary channels having capillary channel surfaces, wherein the capillary channel surfaces of said capillary channels are hydrophilic and capillarity acts as the only force for moving the fluid medium, and wherein each of said first region and said second region comprises a vent;

providing a second substrate; and sealing said second substrate on top of said patterned first substrate, so that said second substrate acts as a cover lid.

16. The method according to claim 15, wherein said second substrate is a hydrophilic film.

* * * * *